(12) United States Patent
Mueller

(10) Patent No.: US 9,492,361 B2
(45) Date of Patent: Nov. 15, 2016

(54) SYSTEM FOR DISSOLUTION OF A TABLET OR GRANULATE IN A STREAM OF WATER

(75) Inventor: Daniel Mueller, Burgstall (IT)

(73) Assignee: Dental Care Innovation GmbH, Nuremberg (DE)

( * ) Notice: Subject to any disclaimer, the term of this patent is extended or adjusted under 35 U.S.C. 154(b) by 0 days.

(21) Appl. No.: 13/520,821

(22) PCT Filed: Mar. 19, 2011

(86) PCT No.: PCT/IB2011/000576
§ 371 (c)(1),
(2), (4) Date: Jul. 6, 2012

(87) PCT Pub. No.: WO2012/127257
PCT Pub. Date: Sep. 27, 2012

(65) Prior Publication Data
US 2014/0120140 A1   May 1, 2014

(51) Int. Cl.
| | | |
|---|---|---|
| A61Q 11/00 | (2006.01) | |
| A61C 17/02 | (2006.01) | |
| A61K 8/11 | (2006.01) | |
| B24C 7/00 | (2006.01) | |
| C11D 17/04 | (2006.01) | |
| C11D 17/00 | (2006.01) | |
| A61C 3/025 | (2006.01) | |
| D06F 39/02 | (2006.01) | |

(52) U.S. Cl.
CPC .............. *A61K 8/11* (2013.01); *A61Q 11/00* (2013.01); *B24C 7/003* (2013.01); *C11D 17/0073* (2013.01); *C11D 17/046* (2013.01); *A61C 3/025* (2013.01); *D06F 39/024* (2013.01); *Y10T 442/10* (2015.04)

(58) Field of Classification Search
CPC ............................. A61C 17/02; A61Q 11/00
See application file for complete search history.

(56) References Cited

U.S. PATENT DOCUMENTS

| | | | |
|---|---|---|---|
| 4,260,054 A | 4/1981 | Bory et al. | |
| 4,308,252 A | 12/1981 | Tomaich et al. | |
| 4,564,005 A | 1/1986 | Marchand et al. | |
| 4,978,297 A * | 12/1990 | Vlock | 433/88 |
| 5,362,472 A | 11/1994 | Lauter et al. | |
| 5,567,389 A * | 10/1996 | Birbara et al. | 422/28 |
| 5,849,253 A | 12/1998 | Crossdale et al. | |
| 6,048,501 A | 4/2000 | Lemaire et al. | |
| 6,301,733 B1 | 10/2001 | Dawson et al. | |
| 7,462,289 B2 | 12/2008 | Ayats et al. | |
| 2007/0184998 A1 | 8/2007 | Evans et al. | |

FOREIGN PATENT DOCUMENTS

| | | |
|---|---|---|
| DE | 3322716 A1 | 1/1985 |
| DE | 3742466 A1 | 6/1989 |
| DE | 4002787 A1 | 8/1991 |
| DE | 19935728 A1 | 2/2001 |
| DE | 102007047478 A1 | 4/2009 |
| DE | 102010051226 A1 | 5/2012 |
| EP | 0628652 A1 | 12/1994 |
| EP | 0691102 A1 | 1/1996 |
| EP | 0839495 A1 | 5/1998 |
| EP | 1072717 A1 | 1/2001 |
| GB | 2334666 A | 9/1999 |
| WO | 2008046580 A1 | 4/2008 |
| WO | WO 2008046580 A1 * | 4/2008 |
| WO | 2011070385 A1 | 6/2011 |

OTHER PUBLICATIONS

International Search Report in corresponding PCT/IB2011/000576 (four pages).

* cited by examiner

*Primary Examiner* — Bethany Barham
*Assistant Examiner* — Peter Anthopolos
(74) *Attorney, Agent, or Firm* — Hooker & Habib, P.C.

(57) ABSTRACT

The application discloses a discus-shaped unit of a tablet or granulates which contain abrasive media, to be dissolved into a stream of water. Tablet or granulates are encased in a flexible, but inherently stable mesh of filaments for to enhance dissolution, avoid clogging nozzles and ease disposal of residues.

7 Claims, 1 Drawing Sheet

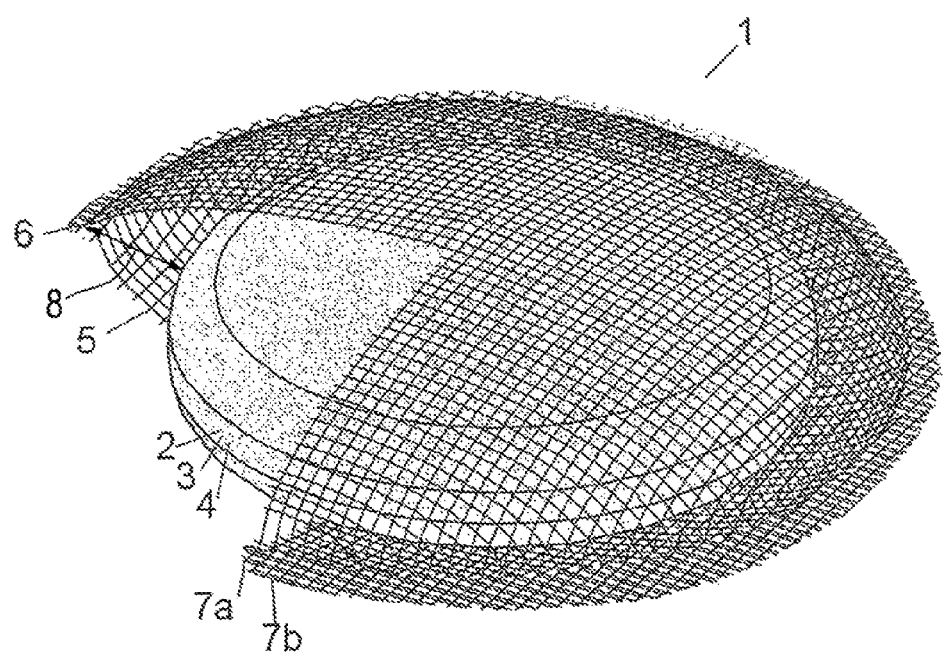

SYSTEM FOR DISSOLUTION OF A TABLET OR GRANULATE IN A STREAM OF WATER

FIELD OF THE INVENTION

The invention relates to a water jet system, wherein media, containing abrasive ingredients, is encased in a mesh of wire or plastic filaments, so to enhance uniform dissolution and avoid re-conglomerations that might clog filters and nozzles.

PROBLEM TO BE SOLVED

For quite a few applications tablets, powders or granulates are used to load water jets or streams with suitable ingredients for cleaning or gardening purposes. Usually mixing chambers are used to hold the tablets or powders, through which a stream of water is directed, that gradually dissolves the media and directs the resulting suspension into a spray nozzle or the like.

There are, however, some drawbacks in most of these systems:
  The dissolution usually tends to be rather irregular. Depending of flow scheme and particular eddies that are difficult to anticipate, tablets ablate differently on their outskirts and powders adhere to some resulting dead sector of the mixing chamber. This demands an augmented volume of water to be injected for total dissolution, which periodically would only inherit at low concentration of the matter. Moreover, the chamber has to be cleaned after use, which is an unpleasant job.
  Partly dissolved ingredients tend to re-agglomerate and might clog filters and nozzles or orifices. This demands a careful selection of the constituent parts and often prohibits a required concentration of matter.
  Abrasive media, which tends to be the most compact part within the mixtures, particularly agglomerate and clog in boundaries of constrictions as a result of their higher density and therefore stronger centrifugal momentum in turbulences and because of their coarser surface.

PRIOR ART

There are quite a few propositions known how to mix ingredients, and particularly abrasive media, into a stream of water. In most cases this is achieved by injecting it into the water stream with gases under pressure, or injecting it under pressure into a mixing chamber as in DE 3742466 A1, DE 4002787 A1, or DE 102007047478 A1, or using other injecting agents, as in U.S. Pat. No. 5,362,472 or foaming additives, as usual in tablets for washing machines (which does not work so well for the heavier abrasive components).

For the dissolution of tablets, some disclosed ideas simply refer to holders of tablets in a water stream (as DE 199 35 728 C2 or EP 95304115.9), which may happen sequentially as to the program of washing machines in DE 97 308 388.4.

Others refer to dispensers, wherein a powder or granulate is gradually released into a stream of water by gravity, as in U.S. Pat. No. 5,849,253, or a tablet is in solution in a periodically flushed secondary reservoir, as in U.S. Pat. No. 6,048,501 and U.S. Pat. No. 7,462,289 B2, or in a gyratory floating dispenser, as in U.S. Pat. No. 6,301,733 B1 and EP 0628652 (A1).

Whereas the first one might be feasible for abrasive media, but quite critical in its handling, the latter require soluble media and the third one is only applicable in rotating drums, like in washing machines.

In statical mixing chambers, as proposed in WO 2008/046580 and DE 3322716 (A1), we particularly found the above mentioned drawbacks of residues in dead sectors and behind constrictions.

A constant decomposition of tablets, powders and granluates containing abrasive matter in mixing chambers therefore had so far not been feasible without serious drawbacks in their possible composition—so to be retraced in application DE 10 2010 051 226.5.

INVENTIVE STEP

Within a suite of studies on performance of abrasive media for dental cleaning, it had been realized, that packing these tablets or powders into a mesh of adequate size can solve the problem:

Firstly it had been recognized, that the mesh provokes a system of small, but equally distributed turbulences in the stream of water around it, thus enhancing the dissolution of the substance quite uniformly, as long as there is adequate space between the tablet or the surface of the powder and the mesh, which was found optimal at approximately 1/10 of the diameter of the tablet or powder surface. This results from a close correlation between particle size of the abrasive medium, the distance and the mesh size. The studies show, that a mesh size of 0.3 mm result in good dissolution behavior, if particle sizes are between 4 and 6 mils, while the tablet is 30 millimeter in diameter and 6 mm thick, whereas clearance between mesh and tablet on the upside is 3.0 Millimeter.

Furthermore the voids within the mesh let small particle of the abrasive media pass easily, whereas larger particle agglomerations cannot enter the stream of slurry.

Deduced from this finding was the solution, that residual materials, as firmly cemented abrasive particles, may be kept within the mesh and can easily be disposed with it after use.

SUMMARY OF THE INVENTION

Assessing the aforementioned findings, the invention refers to a tablet or granulate comprising abrasive media, encased in a flexible, but sufficiently stiff mesh and exposed to a water stream, that would dissolve soluble components and carry away the detached abrasive particles in a stream of slurry, whereas inevitably cemented residues can be disposed with the mesh.

The mesh may be part of a system for dissolution of a tablet or granulate in a stream of water, including a tablet or granulate fully encased in the flexible, but inherently stable mesh. The natural resonance of the mesh, in possible embodiments, may be between 60 Hz and 500 Hz when the mesh is submerged in water.

The tablet or granulate may include abrasive media together with other ingredients. The multiplicity of the voids within the mesh provoke multiple turbulence to assist in forming a stream or slurry of detached abrasive particles from the tablet or granulate.

The mesh may be formed like a discus. The mesh may be welded to form a rimlike bearing around the discus.

In possible embodiments, a clearance of between 1/20th and 1/10th of its diameter between the tablet's face or an equivalent straightening of the granulate and the mesh. In other possible embodiments, the mesh size does not exceed 0.3 mm. In yet other possible embodiments the mesh may be made of filament having a filament diameter of between 0.12 mm and 0.25 mm.

The mesh may be made of nylon or similar thermoplastics. In yet other embodiments the mesh may be made of a bio-plastic, such as a cellulosic acid ester or a lactic acid.

PREFERRED EMBODIMENT

The dissolution works particularly well, as long as the mesh is kept in some distance from pressed tablets, or if granulates are kept sufficiently loose within the mesh.

As an optimal form a disk-like mesh structure could be found, wherein a tablet can float in a vertical water stream without turning and aligning to the stream.

Therefore, with respect to easy manufacturing, a preferable embodiment of the invention is a disc-like mesh, that results from a double layer of mesh with a tablet or small heap of Granulate disposed in between, that is circumferentially welded together to form a rim of a few millimeter width, which is used as bearing area.

The continuous delivery of the abrasive component creates a suspension flow wherein particle agglomerates do not exceed a size of 0.3 mm. That remains quite constant within the period of the dissolution, as long as sufficient abrasive particles are present within the mesh.

Secondly, re-agglomerations that occur are held within the mesh and tend to dissolve again in the current, before they can clog filters and orifices. This helps to provide a rather uniform concentration of media within the stream of water, particularly after the substance is reduced at the end—it then typically is forming a cloud of media in the mesh, that finally is carried away quite abruptly.

A suspension stream, thus controlled by the mesh will pass through curved nozzles (30° curvature at the nozzle point) without clogging it, due to the continuous flow pattern of the suspension.

Residues that cannot dissolve and adhering agglomerations need not to be removed by scratching it out of the mixing chamber, but can easily be disposed by simply opening and tilting the unit to let the mesh with all residues fall off.

DESCRIPTION OF THE DRAWING

FIG. 1 shows—in a cut-off view—a tablet 1 containing abrasive particles 2-4, encased in a mesh, that consists of two dish-like cups 5 and 6, which are formed by welding a rim 7a and 7b between two meshes. The mesh encloses a volume larger than the volume of the tablet, the mesh and the tablet cooperatively defining a clearance dimension 8 in which the mesh is spaced away from an outside surface of the tablet if the tablet were centered in the mesh as shown in the drawing. The clearance dimension may, in embodiments, be between $1/10$ and $1/20$ of the tablet diameter.

What is claimed is:

1. An article for insertion in a water-conveying dental cleaning device, the article comprising a water-dispersible dental cleaning tablet that comprises abrasive particles, the tablet being enclosed in a hollow water-permeable discus having a circumferential rim, the discus comprising a first concave mesh and an opposing second concave mesh.

2. The article of claim 1, wherein the screen size of the mesh material that forms the first concave mesh and the opposing second concave mesh does not exceed 0.3 mm.

3. The article of claim 1, wherein the first concave mesh and the opposing second concave mesh are made of a thermoplastic material.

4. The article of claim 1, wherein the first concave mesh and the opposing second concave mesh are made of a bioplastic material.

5. The article of claim 1, wherein the volume of the interior space defined by the discus is greater than the volume of the tablet, the difference in volume being defined by an annular space that surrounds the periphery of the tablet and borders the circumferential rim of the discus.

6. The article of claim 1, wherein the first concave mesh and the opposing second concave mesh are formed of filament having a thickness of between 0.12 mm and 0.25 mm.

7. The article of claim 1, wherein the first concave mesh comprises a first annular rim, the opposing second concave mesh comprises a second annular rim, and the circumferential rim of the discus is made by attaching the first annular rim to the second annular rim.

* * * * *